US 8,679,125 B2

(12) United States Patent
Smith et al.

(10) Patent No.: US 8,679,125 B2
(45) Date of Patent: Mar. 25, 2014

(54) ROBOTIC GUIDED FEMORAL HEAD RESHAPING

(75) Inventors: Aaron P. Smith, Warsaw, IN (US); Jason D. Meridew, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 637 days.

(21) Appl. No.: 12/888,011

(22) Filed: Sep. 22, 2010

(65) Prior Publication Data
US 2012/0071893 A1    Mar. 22, 2012

(51) Int. Cl.
*A61B 17/00*    (2006.01)

(52) U.S. Cl.
USPC .............................. 606/81; 606/79

(58) Field of Classification Search
USPC .................................... 606/86 R, 89
See application file for complete search history.

(56) References Cited

U.S. PATENT DOCUMENTS

| | | | |
|---|---|---|---|
| D604,753 | S | 11/2009 | Suarez et al. |
| 7,623,702 | B2 | 11/2009 | Arata et al. |
| 2006/0142657 | A1 | 6/2006 | Quaid et al. |
| 2006/0155380 | A1 | 7/2006 | Clemow et al. |
| 2006/0190086 | A1 | 8/2006 | Clemow et al. |
| 2007/0142751 | A1 | 6/2007 | Kang et al. |
| 2007/0219639 | A1 | 9/2007 | Otto et al. |
| 2007/0255412 | A1 | 11/2007 | Hajaj et al. |
| 2007/0260256 | A1 | 11/2007 | Beaule |
| 2007/0270685 | A1 | 11/2007 | Kang et al. |
| 2007/0296366 | A1 | 12/2007 | Quaid et al. |
| 2008/0004633 | A1 | 1/2008 | Arata et al. |
| 2008/0010705 | A1 | 1/2008 | Quaid et al. |
| 2008/0010706 | A1 | 1/2008 | Moses et al. |
| 2008/0033571 | A1 | 2/2008 | Tuke |
| 2008/0058945 | A1 | 3/2008 | Hajaj et al. |
| 2008/0161829 | A1 | 7/2008 | Kang |
| 2008/0262812 | A1 | 10/2008 | Arata et al. |
| 2008/0281343 | A1 | 11/2008 | Dewey et al. |
| 2009/0012532 | A1* | 1/2009 | Quaid et al. ................ 606/130 |
| 2009/0149965 | A1 | 6/2009 | Quaid |
| 2009/0192620 | A1 | 7/2009 | Ebbitt |
| 2009/0209884 | A1 | 8/2009 | Van Vorhis et al. |
| 2009/0228111 | A1 | 9/2009 | Otto |
| 2009/0306499 | A1 | 12/2009 | Van Vorhis et al. |
| 2009/0314925 | A1 | 12/2009 | Van Vorhis et al. |
| 2009/0324078 | A1 | 12/2009 | Wu et al. |

OTHER PUBLICATIONS

"Amazing Precision. Beautiful Results. The next evolution of MAKOplasty® is here." MAKO Surgical Corp. Feb. 2009.
"Are You Living with Knee Pain?" MAKO Surgical Corp.® Oct. 2009.

* cited by examiner

*Primary Examiner* — Sameh Boles
(74) *Attorney, Agent, or Firm* — Harness, Dickey

(57) ABSTRACT

A method of performing hip surgery with a robotic guided system on a patient with femoral acetabular impingement can include identifying the femoral acetabular impingement on the patient. Data related to a proximal femur and an acetabulum of the patient is acquired. A three-dimensional model of at least one of the patient's proximal femur and acetabulum is created based on the data acquired. A location and amount of bone to be removed is determined. Dynamic movement limits of a cutting tool associated with the robotic guided system is set based on the determination. The determined bone of at least one of the proximal femur and acetabulum is removed with the tool while being inhibited from moving the tool outside of the dynamic limit by the robotic guided system.

14 Claims, 3 Drawing Sheets

ROBOTIC GUIDED FEMORAL HEAD RESHAPING

FIELD

The present disclosure relates to a method of performing hip surgery, and more specifically to a method of performing hip surgery with a robotic guided system on a patient with femoral acetabular impingement.

BACKGROUND

This section provides background information related to the present disclosure which is not necessarily prior art.

Femoral acetabular impingement can occur when a portion of a proximal femur rubs unfavorably against an acetabulum. One form of femoral acetabular impingement is called "cam impingement" where a portion of bone protrudes on a proximal femur generally at a location on the femur where the femoral head and neck meet. The protrusion, in some instances, can rub excessively against the acetabulum. Another kind of femoral acetabular impingement called "pincer impingement" can occur where a portion of bone protrudes on an anterior rim of the acetabulum. The protrusion on the acetabulum can block normal movement of the proximal femur. It is also possible to have a combination of both cam and pincer impingement on a given patient's hip. Femoral acetabular impingement can cause intermittent groin or hip pain that can intensify over time.

In some instances, it may be desirable to cut away or burr the protruding bone on the proximal femur and/or acetabulum. In one method, a surgeon can cut away the identified protruding bone with a tool, such as a burr that is negotiated freehand by a surgeon. In some instances, relying on a surgeon's freehand movement of such a cutting tool can result in removing too much or not enough bone. In this regard, removing too much bone from the proximal femur can compromise the integrity of the proximal femur and may lead to a greater risk of femoral neck fracture. Moreover, in some examples, a surgeon does not remove enough bone, which can lead to future impingement problems.

SUMMARY

This section provides a general summary of the disclosure, and is not a comprehensive disclosure of its full scope or all of its features.

A method of performing hip surgery with a robotic guided system on a patient with femoral acetabular impingement can include identifying the femoral acetabular impingement on the patient. Data related to a proximal femur and an acetabulum of the patient is acquired. A three-dimensional model of at least one of the patient's proximal femur and acetabulum is created based on the data acquired. A location and amount of bone to be removed can be determined. Dynamic movement limits of a cutting tool associated with the robotic guided system is set based on the determination. The determined bone of at least one of the proximal femur and acetabulum is removed with the tool while being inhibited from moving the tool outside of the dynamic limit by the robotic guided system.

According to additional features, identifying the femoral acetabular impingement can include identifying at least one of a protrusion on the proximal femur and a protrusion on the acetabulum. The protrusion on the proximal femur can comprise a protrusion at an intersection of a femoral head and a femoral neck of the proximal femur. The protrusion on the acetabulum can comprise a protrusion on an anterior rim of the acetabulum. Acquiring the data can include touching at least one of the proximal femur and the acetabulum of the patient at a plurality of locations with a pointing tool associated with the robotic guided system. Touching at least one of the proximal femur and the acetabulum can comprise touching at least one of the proximal femur and the acetabulum with a stylus associated with the robotic guided system.

According to additional features, the pointing tool can be coupled to a robotic arm of the robotic guided system. At least one of the proximal femur and the acetabulum of the patient can be subsequently touched with the pointing tool. The pointing tool can be subsequently removed from the robotic arm. The cutting tool can be subsequently coupled to the robotic arm. The identified bone can be subsequently removed with the cutting tool. Identifying the femoral acetabular impingement can comprise acquiring medical imaging of the proximal femur and the acetabulum of the patient. According to other features, acquiring medical imaging can comprise performing at least one of an x-ray and a magnetic resonance imaging. Removing the determined bone with the cutting tool can comprise removing the determined bone with a burr disposed on the cutting tool.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 3:
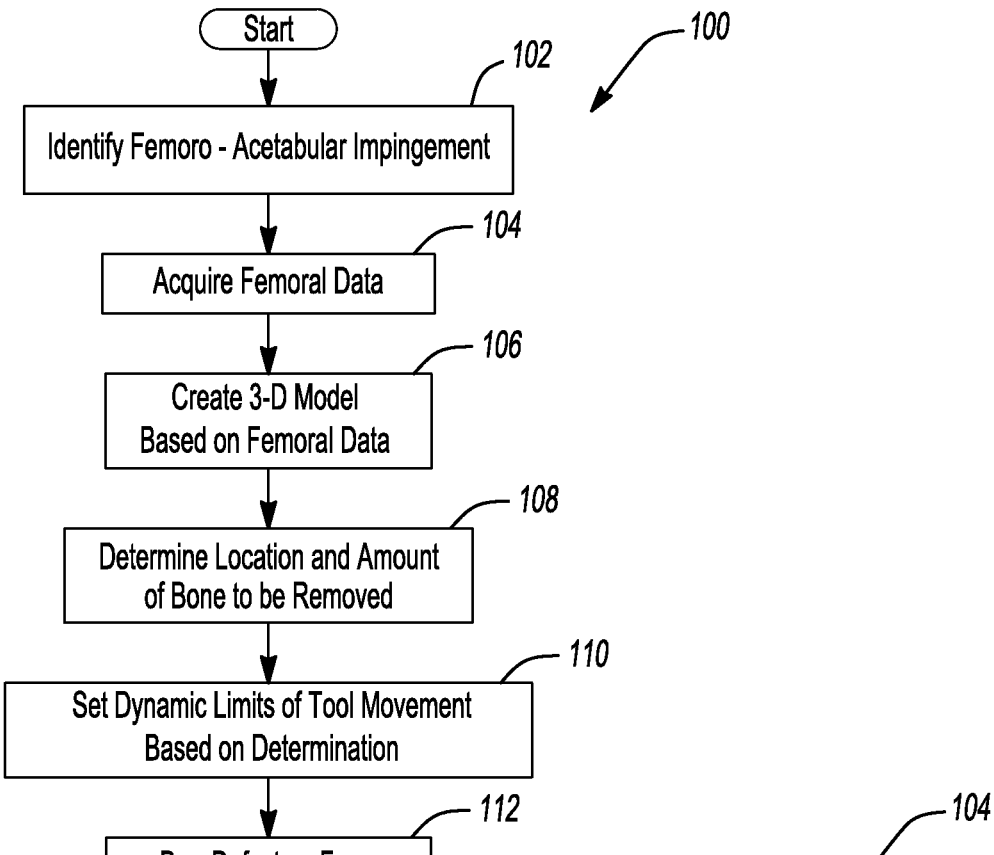
Figure 4:
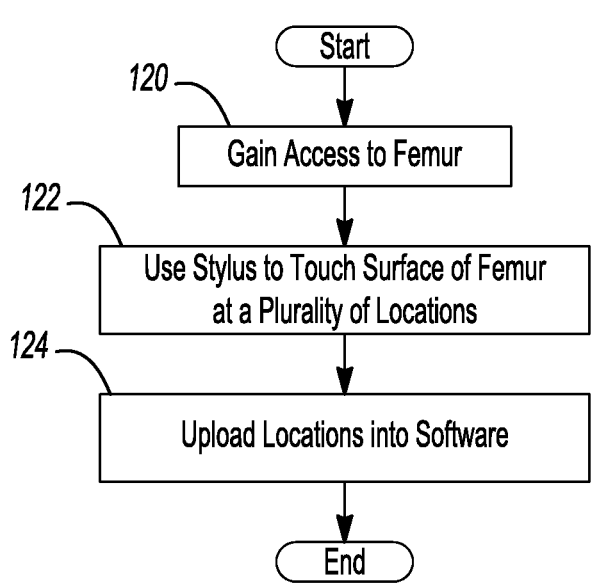

FIG. 3 is a flow chart illustrating an exemplary method of performing hip surgery with the robotic guided system on a patient with femoral acetabular impingement according to one example of the present teachings; and FIG. 4 is a flow chart illustrating an exemplary method of acquiring data related to the femoral head and acetabulum of the patient with the robotic guided system according to one example of the present teachings.

Corresponding reference numerals indicate corresponding parts throughout the several views of the drawings.

DETAILED DESCRIPTION

Example embodiments will now be described more fully with reference to the accompanying drawings.

Figure 1:
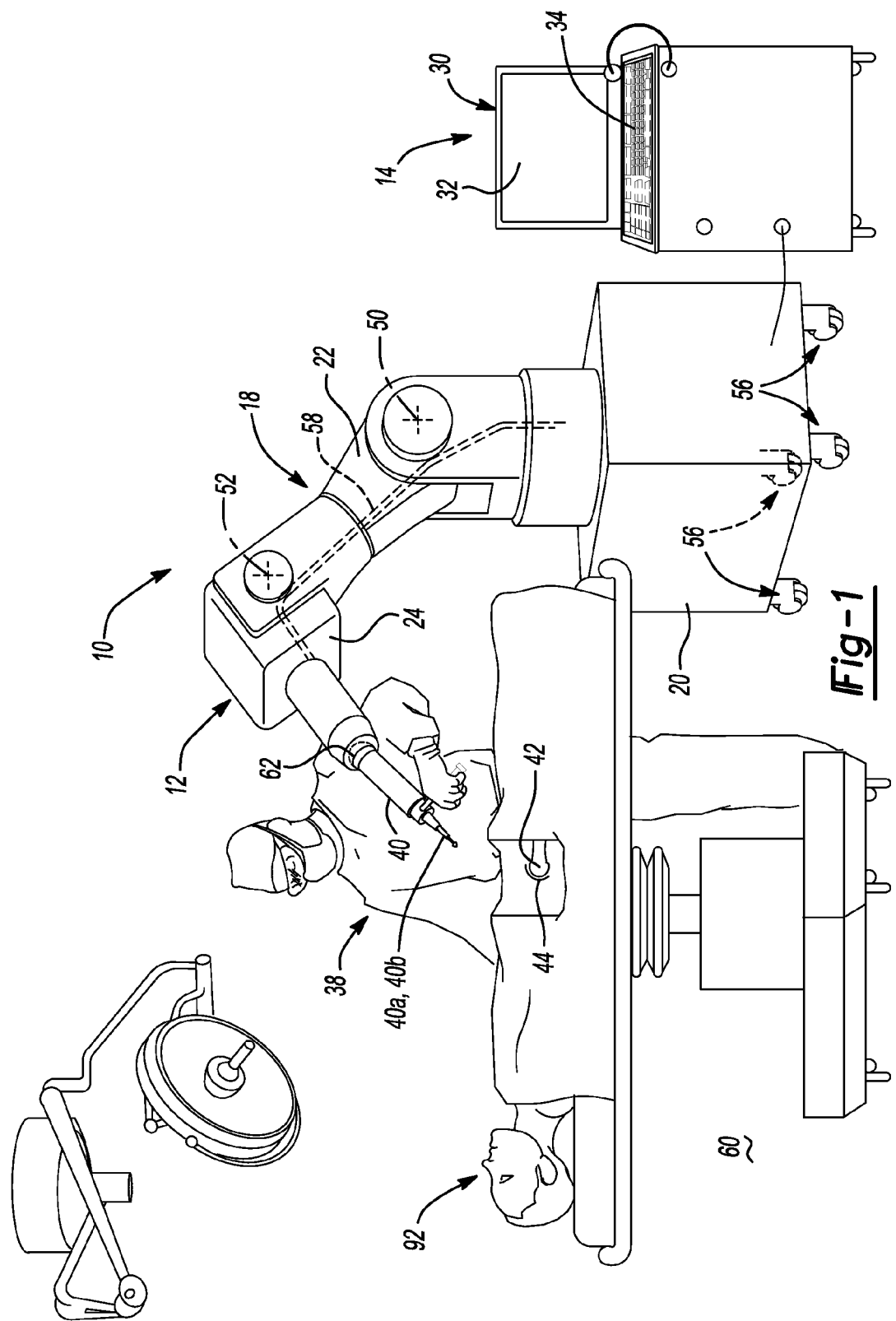
FIG. 1 is an exemplary environmental view illustrating a surgeon performing hip surgery on a patient with femoral acetabular impingement and using a robotic guided femoral head/acetabulum reshaping system according to one example of the present teachings.

With initial reference to FIG. 1, a robotic guided femoral head/acetabulum reshaping system according to one example of the present teachings is shown and generally identified at reference numeral 10. The robotic guided femoral head/acetabulum reshaping system 10 can generally comprise a surgical tool guiding device 12 and a computing system or work station 14. The surgical tool guiding device 12 can generally comprise a robotic arm 18 that can provide selective dynamic movement relative to a base 20. The robotic arm 18 can generally include a first arm portion 22 and a second arm portion 24. The computing system 14 can generally comprise a computer or processor 30 having a display 32 and an input device 34. The computing system 14 can communicate with the surgical tool guiding device 12, as will become appreciated from the following discussion. As will be described in greater detail herein, a surgeon 38 can use the surgical tool guiding device 12 of the robotic guided femoral head/acetabulum reshaping system 10 to limit or control a dynamic range of movement permitted by a surgical tool 40 that is coupled to the robotic arm 18. In this regard, the surgical tool guiding device 12 can inhibit movement of the surgical tool 40 in such a way as to confine any cutting or burring of a femoral head 42 and/or an acetabulum 44 within a pre-determined boundary.

The surgical tool guiding device 12 will now be described in greater detail. The first arm portion 22 can be generally movably coupled to the base 20 through a first joint 50. The second arm 24 can be generally movably coupled to the first arm portion 22 through a second joint 52. The base 20 can generally include a plurality of wheels 56 that can be selectively locked to immobilize the base 20 relative to a floor 60. In other examples, the base 20 can be configured to directly sit on the floor 60 or alternatively include legs or other members that can support the base 20 relative to the floor 60. A distal end of the second arm portion 24 can include a coupling 62. The coupling 62 can be manipulated for selectively coupling to various instruments or surgical tools 40. The instruments or tools can include, but are not limited to, a stylus 40a, and a cutting tool 40b, such as a burring instrument.

In various examples, the first joint 50 can provide translation and/or rotation of the first arm portion 22 relative to the base 20. The second joint 52 can provide translation and/or rotation of the second arm 24 relative to the first arm portion 22. A hydraulic system 58 can be disposed throughout the surgical tool guiding device 12. For example, the hydraulic system 58 can cooperate with the first arm portion 22 and/or the second arm portion 24 to confine movement of the robotic arm 18 within an allowed pre-defined range of motion as will be described in detail herein. For example, the hydraulic system 58 route hydraulic fluid to areas that can freeze or lock selected components of the surgical tool guiding device 12 to preclude unwanted advancement of the surgical tool 40 beyond the identified allowed or pre-determined range of motion. Other mechanisms can be incorporated on the robotic arm 18 to assist in controlling or limiting movement of the robotic arm 18. Furthermore, it can be appreciated that while the robotic arm 18 has been described as having two arm portions that move relative to each other and a base, other configurations may be provided.

Figure 2:
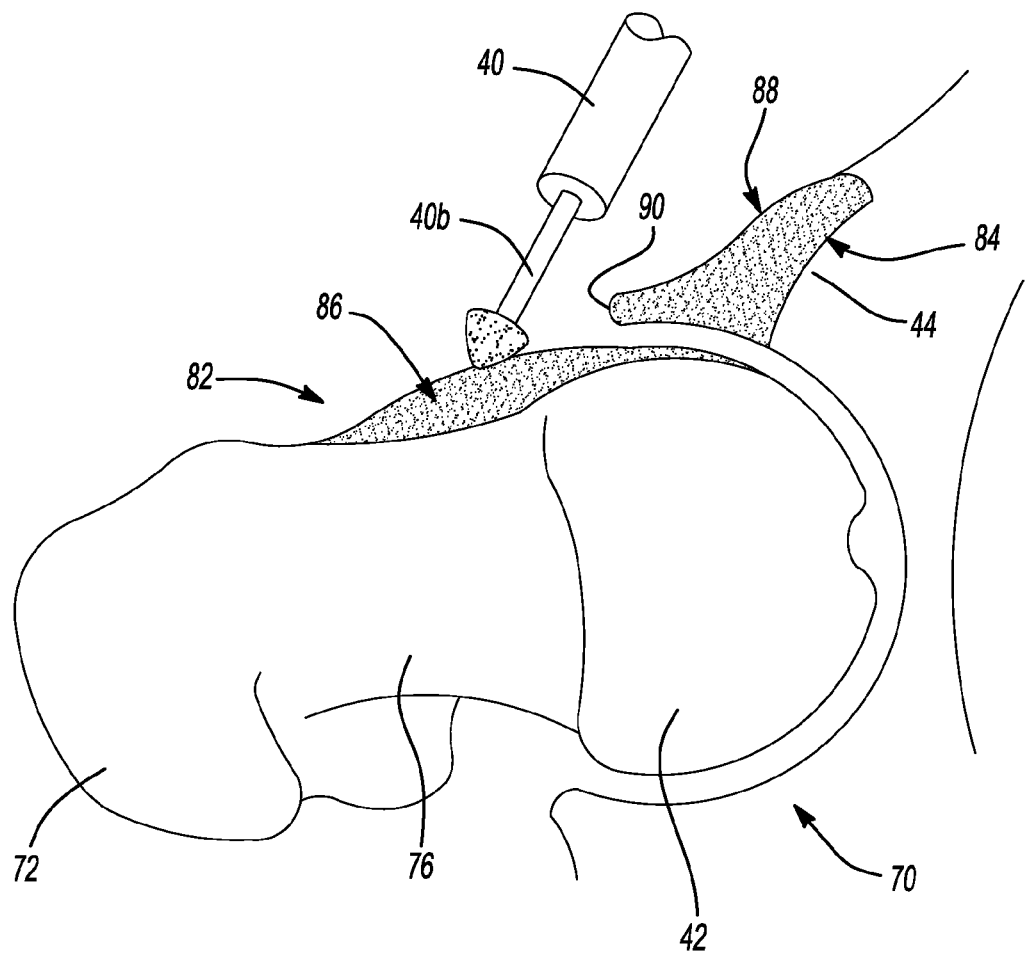
FIG. 2 is a superior view of an exemplary hip joint of a patient illustrating an exemplary femoral protrusion on a patient's femoral head and an acetabular protrusion on the patient's acetabulum.

With additional reference now to FIG. 2, an exemplary hip joint 70 having femoral acetabular impingement is shown. The hip joint 70 generally includes a proximal femur 72 having the femoral head 42 and a femoral neck 76. The hip joint 70 further comprises the acetabulum 44 that receives the femoral head 42. The exemplary hip joint 70 has a femoral acetabular impingement condition caused collectively by a cam impingement 82 and a pincer impingement 84. The cam impingement 82 can be generally caused by a femoral protrusion 86 formed at an area where the femoral head 42 and the femoral neck 76 meet. The pincer impingement 84 can be generally caused by an acetabular protrusion 88 formed on an anterior rim 90 of the acetabulum 44. It will be appreciated that while the exemplary hip joint 70 is shown having both of a cam impingement 82 and a pincer impingement 84 that the hip joint 70 may alternatively comprise only one of the cam impingement 82 and pincer impingement 84 that cause femoral acetabular impingement.

With further reference now to FIG. 3, an exemplary method of performing hip surgery with the robotic guided system 10 on a patient 92 with femoral acetabular impingement is shown and generally identified at reference numeral 100. In block 102, the surgeon 38 can identify the femoral acetabular impingement. According to various examples, the surgeon 38 can identify the femoral acetabular impingement by medical imaging, such as, but not limited to, an x-ray, a computerized axial tomography scan or a magnetic resonance imaging procedure. The medical imaging procedure can produce an image, such as illustrated in FIG. 2 where a surgeon can identify the femoral protrusion 86 and/or the acetabular protrusion 88 as part of an initial broad identification step.

In block 104, the surgeon 38 can acquire data related to the femoral head 42, femoral neck 76 and/or the acetabulum 44. According to one example of the present teachings, the surgeon 38 can utilize the stylus 40a with the surgical tool 40. The stylus 40a can be attached to the tool 40 of the robotic arm 18. The surgeon 38 can move the stylus 40a and touch a distal tip of the stylus 40a to a plurality of locations on the femoral head 42, femoral neck 76 and/or the acetabulum 44. Each time the distal tip of the stylus 40a touches the femoral head 42, femoral neck 76 and/or the acetabulum 44, a reference point in space can be communicated from the surgical tool guiding device 12 to the computing system 14 based on sensors in the linkages 50 and 52. In some examples, the data acquired with the stylus 40a can be used to verify the image data obtained during the medical imaging procedure.

In block 106, software of the computing system 14 can be used to create a three-dimensional model of the patient's hip joint 70 based on the plurality of data points corresponding to contacting the surface of the femoral head 42, femoral neck 76 and acetabulum 44 from the stylus 40. In other features, the three-dimensional model of the patient's hip joint can be created from the medical imaging procedure.

In block 108, the surgeon 38 can use the computing system 14 to reference the three-dimensional model to determine and verify the location and amount of bone (e.g., femoral protrusion 86 and/or acetabular protrusion 88) to be removed relative to the 3-D model. In some examples, a surgeon can reference an image on the display 32 and use the input device 34 to draw or mark on the image the areas of bone to be removed. Once the location and amount of bone that is to be removed has been determined, software in the computing system 14 can be used to set dynamic movement limits of the tool 40 based on the marked image. In other examples, the dynamic movement limits can be automatically set based on a pre-operative determination of the bone to be removed.

In this regard, movement of the surgical tool 40 can be restricted to areas in space that correspond with locations in space having the femoral protrusion 86 and/or the acetabular protrusion 88. The surgical tool 40 can therefore be inhibited from moving into areas in space that correspond to healthy bone and/or tissue, etc. In this regard, the computing system 14 can communicate with the hydraulic system 58 of the surgical tool guiding device 12 to set limits on the dynamic movement of some or all of the components in the robotic arm 18, such that the robotic arm 18 (or portions thereof) freezes, restricts or prevents movement of the surgical tool 40 when the surgeon 38 attempts (purposely or inadvertently) to move the surgical tool 40 outside of the established boundary. In one example, the surgeon 38 can remove the stylus 40a from the coupling 62 and replace it with the cutting tool 40b, such as a burring instrument. In block 112, a surgeon 38 can use the cutting tool 40b to cut away or burr the femoral protrusion 86 and/or the acetabular protrusion 88 while being inhibited from moving the cutting tool 40b outside of the dynamic limit established by the computing system 14.

As can be appreciated, the robotic guided femoral head/acetabulum reshaping system 10 can be particularly useful to a surgeon 38 by precluding the surgeon 38 from inadvertently moving the cutting tool 40b too far into bone of the proximal femur 72 and/or the acetabulum 44. Therefore, the robotic guided femoral head/acetabulum reshaping system 10 can assist a surgeon 38 in guiding the cutting tool 40b three-dimensionally, such that it is confined to cut bone only in identified areas of a femoral protrusion 86 and/or an acetabular protrusion 88 to obtain a natural shaped femoral acetabular substantially spherical joint.

Turning now to FIG. 4, the step of acquiring data related to the femoral head 42, femoral neck 76 and/or acetabulum 44 identified in block 104 will be further described. In block 120, a surgeon 38 can gain access to a patient's femur/acetabulum. A surgeon 38 can use any known technique or procedure, such as providing a single or a collection of entry points through a patient's skin to suitably access the proximal femur 72 and the acetabulum 44. In block 122, the surgeon 38 can use the stylus 40a to touch the surface of the proximal femur 72 and/or the acetabulum 44. In block 124, the plurality of locations in space corresponding to the surfaces touched by the stylus 40a are uploaded into software in the computing system 14. The software can convert the plurality of locations in space into a three-dimensional model of the patient's hip joint 70.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of performing hip surgery with a robotic guided system on a patient, the method comprising:
   identifying a femoral acetabular impingement on the patient;
   touching at least one of proximal femur and acetabulum of the patient at a plurality of locations with a stylus coupled to a robotic arm associated with the robotic guided system and acquiring a plurality of corresponding data;
   creating a three-dimensional model of at least one of the patients' proximal femur and acetabulum based on the plurality of data acquired by touching;
   determining a location and amount of bone to be removed;
   creating a boundary or model of a desired shape of at least one of the proximal femur and acetabulum;
   setting dynamic movement limits of a cutting tool associated with the robotic guided system based on the determination; and
   removing the determined bone of at least one of the proximal femur and acetabulum with the tool while being inhibited from moving the tool outside of the dynamic limit by the robotic guided system.

2. The method of claim 1 wherein identifying the femoral acetabular impingement includes identifying at least one of a protrusion on the proximal femur and a protrusion on the acetabulum.

3. The method of claim 2 wherein identifying the femoral acetabular impingement includes identifying a protrusion at an intersection of a femoral head and a femoral neck of the proximal femur.

4. The method of claim 3 wherein identifying the femoral acetabular impingement includes identifying a protrusion on an anterior rim of the acetabulum.

5. The method of claim 1 wherein removing the determined bone with the cutting tool comprises removing the determined bone with a burr disposed on the cutting tool.

6. A method of performing hip surgery with a robotic guided system on a patient, the method comprising:
   acquiring a medical image of at least one of a proximal femur and an acetabulum of the patient;
   identifying a femoral acetabular impingement on the patient based on the medical image;
   touching at least one of a proximal femur and acetabulum of the patient at a plurality of locations with a stylus coupled to a robotic arm associated with the robotic guided system and acquiring corresponding data;
   creating a three-dimensional model with a workstation of the robotic guided system of at least one of the proximal femur and acetabulum of the patient based on the plurality of data acquired by touching;
   determining a location and amount of bone to be removed with the workstation;
   creating a boundary or model of a desired shape of the proximal femur;
   setting dynamic movement limits of a cutting tool associated with the robotic guided system based on the determination;
   removing the stylus from the robotic arm and subsequently coupling a cutting tool to the robotic arm; and
   removing the determined bone with the tool while being inhibited by the robotic arm from moving the tool outside of the dynamic limit.

7. The method of claim 6 wherein identifying the femoral acetabular impingement includes identifying at least one of a protrusion on the proximal femur and a protrusion on the acetabulum.

8. The method of claim 7 wherein identifying the femoral acetabular impingement includes identifying a protrusion at an intersection of a femoral head and a femoral neck of the proximal femur.

9. The method of claim 8 wherein identifying the femoral acetabular impingement includes identifying a protrusion on an anterior rim of the acetabulum.

10. The method of claim 6 wherein acquiring medical imaging comprises performing at least one of an x-ray and a magnetic resonance imaging.

11. The method of claim 6 wherein removing the determined bone with the cutting tool comprises removing the determined bone with a burr disposed on the cutting tool.

12. A method of performing hip surgery with a robotic guided system on a patient, the method comprising:
   acquiring a medical image of the proximal femur of the patient;
   identifying a femoral acetabular impingement on the patient based on the medical image;
   touching a femoral head and neck of the proximal femur of the patient at a plurality of locations with a stylus coupled to a robotic arm associated with the robotic guided system and acquiring a plurality of corresponding data;

creating a three-dimensional model with the robotic guided system of the proximal femur of the patient based on the plurality of data acquired by touching;

determining a location and amount of bone to be removed on the proximal femur of the patient;

creating a boundary or model of a desired shape of the proximal femur;

setting dynamic movement limits of a cutting tool associated with the robotic guided system based on the determination;

removing the stylus from the robotic arm and subsequently coupling a cutting tool to the robotic arm; and removing the determined bone with the tool while inhibiting the robotic arm from moving the tool outside of the dynamic limit.

13. The method of claim 12 wherein identifying the femoral acetabular impingement includes identifying a protrusion on the proximal femur.

14. The method of claim 13 wherein identifying the femoral acetabular impingement includes identifying a protrusion at an intersection of a femoral head and a femoral neck of the proximal femur.

\* \* \* \* \*